United States Patent
Khowdairy

(10) Patent No.: US 10,118,893 B2
(45) Date of Patent: Nov. 6, 2018

(54) METHOD OF MAKING COMPLEX NANO PARTICLES AND USING THE SAME TO REDUCE CELL VIABILITY

(71) Applicant: Umm Al-Qura University, Makkah (SA)

(72) Inventor: Manal Mohamed Khowdairy, Makkah (SA)

(73) Assignee: Umm-Al-Qura University, Makkah (SA)

( * ) Notice: Subject to any disclaimer, the term of this patent is extended or adjusted under 35 U.S.C. 154(b) by 0 days.

(21) Appl. No.: 14/500,544

(22) Filed: Sep. 29, 2014

(65) Prior Publication Data

US 2016/0297847 A1    Oct. 13, 2016

(51) Int. Cl.
*C07F 9/02* (2006.01)
*C07C 391/00* (2006.01)

(52) U.S. Cl.
CPC .................. *C07C 391/00* (2013.01)

(58) Field of Classification Search
CPC .............................. C07H 23/00; C07C 391/00
USPC ........................................ 558/136
See application file for complete search history.

(56) References Cited

PUBLICATIONS

Badawi et al., J Surfact Deterg (2007) 10:257-267.*

* cited by examiner

*Primary Examiner* — Clinton Brooks
*Assistant Examiner* — Kofi Adzmali
(74) *Attorney, Agent, or Firm* — Geeta Kadambi; Riddhi IP LLC

(57) ABSTRACT

The development of anticancer metal-based drugs was done by reacting oyelamine with selenous acid to produce a quaternary ammonium salt which consequently converted to platinum and cobalt cationic complexes via complexing the first compounds with platinum (II) or cobalt (II) ions. The surface properties studies that were conducted included critical micelle concentration (CMC), maximum surface excess (Γmax) and minimum surface area (Amin). Free energy of micellization ($\Delta G°$ mic) and adsorption ($\Delta G°$ ads) were calculated. Antitumor activities were tested by using Ehrlich Acites Carcinoma (EAC) as a model system of mice cell tumor. These compounds were also tested in vitro on human five monolayer tumor cell lines: MCF7 (Breast carcinoma), HEPG2 (liver carcinoma), and HCT116 (colon carcinoma), etc. FTIR spectra, elemental analysis and H1 NMR spectrum were performed to insure the purity of the prepared compounds.

10 Claims, 1 Drawing Sheet

METHOD OF MAKING COMPLEX NANO PARTICLES AND USING THE SAME TO REDUCE CELL VIABILITY

FIELD OF TECHNOLOGY

This disclosure relates generally to a method of making a complex nano particle and using the same to reduce cell viability. More specifically Cobalt and/or Platinum are used with oyelammonium hydrogen selenite to form a complex that would be used to reduce tumor size or bacterial growth by reducing cell viability.

BACKGROUND

Cationic surfactants have been the focus of wide spread interest over decades due to their ability to self-assemble in super molecular structures such as micelles. The aggregates formed create sharp polarity gradients at the interface and define clear hydrophobic regions in an aqueous solution. Those properties are of fundamental importance for the creation of new materials.

Surfactant metal complexes are expected to provide a wide range of interesting phenomena on the aggregation behavior in aqueous solution due to a variety of their charge numbers, size and extent of hydrophopicity by a combination of a central metal and ligands. However, their physical properties in solutions have not been extensively studied. In the studies so far performed, novel characters of surfactant metal complexes have been revealed, and the results should provide significant information on surfactant solution chemistry. Metaloaggregates are made of surfactants that combine a metal-coordinating polar head to hydrophobic tail. The polar head of the surfactant is functionalized with metal ions are bound to and surrounded by hydrophobic region, similar to the situation found in metalloproteinase. The antimicrobial action of cationic surfactant is based on their ability to disrupt the integral bacterial membrane by a combined hydrophobic and electrostatic adsorption phenomenon at the membrane water interface making disorganization. The pathogenic bacterial cell membrane is predominantly negatively charged as compared with eukaryotic cells. Hence the positive charge of the cationic amphiphile facilitates their interactions with bacterial membrane.

The main goal of cancer therapy is to attain maximum therapeutic damage of tumor cells in combination with minimum concentration of the drug. This can be achieved in principle via selective antitumor preparations, the cytostatic effects of which would be restricted within tumor tissue. While 100% selectivity may be impractical, achievement of reasonably high selectivity seems to be a feasible aim. The bioenergetic status in tumor was selective and affected by the Metal complexes. Minimization of signals of high-energy phosphate was observed after injection of the complexes. An increase of the number of DNA single-strand breaks registered in tumor tissue, supporting the suggestion that complexes may directly affect DNA, but the action of these complexes as antitumor agents found to be dependent on the type of tumer cell line tested.

SUMMARY

The invention discloses a method of making and using a complex nano particle as antitumor agent. More specifically Cobalt and/or Platinum are used with olylammonium hydrogen selenite as complex to reduce cell viability.

In one embodiment, a method of making the olylammonium hydrogen selenite is described. In another embodiment, a method of making the complex of olylammonium hydrogen selenite and Cobalt (Co) is described. In another embodiment, a method of making the complex of olylammonium hydrogen selenite and Platinum (Pt) is described.

In one embodiment, nanoparticle comprising of cyclodextrin and Co/Pt complex is described. In another embodiment, characterization of the nanoparticle (cyclodextrin and Co/Pt complex) is performed to prove superior functional qualities of the nanoparticle.

In one embodiment, cancer cell lines of various concentration and types were treated with nanoparticle comprising of cyclodextrin and Co/Pt complex and antitumor activity were observed. In one embodiment, growth of bacteria is reduced by reducing the cell viability using nanoparticle comprising of cyclodextrin and Co/Pt complex.

Other features will be apparent from the accompanying drawings and from the detailed description that follows.

BRIEF DESCRIPTION OF THE DRAWINGS

Example embodiments are illustrated by way of example and not limitation in the figures of the accompanying drawings, in which like references indicate similar elements and in which:

FIG. 1 shows the picture of nanoparticle comprising of cyclodextrin andolylammonium hydrogen selenite Co complex using Transmission Electron Microscopy (TEM).

Other features of the present embodiments will be apparent from the accompanying the detailed description that follows.

DETAILED DESCRIPTION

In this invention a method to make the nanoparticle comprising of olylammonium hydrogen selenite and Co/Pt complex is discussed. The method of using the nanoparticle comprising of olylammonium hydrogen selenite and Co/Pt complex for inhibition of cell viability in mammalian cells as well as bacterial cell are disclosed.

Synthesis of Olylammonium Hydrogen Selenite:

All chemicals used here were bought from Sigma Aldrich USA. One mole of selenous acid was mixed with one mole of oyelamine at room temperature in ethyl alcohol to make a mixture. The mixture was stirred until the formation of precipitate slowed down or stopped. One can visually ascertain the slowing of precipitate formation or stopping of the precipitate formation due to color formation of the precipitate. The (white yellowish, reddish and pink) precipitate (precipitate 1) was filtered and washed by ethyl alcohol, then recrystallized by adding diethyl ether (precipitate 2).([17]) The precipitate 2 (designated as $II_a$) has the general formula as follows:

$$RN^{+}H_3HSeO_3 \text{ (where R=olyl)} \quad \text{(Eq 1)}$$

Synthesis of metal complexes: Synthesis of cobalt (II) or platinum hydrogen selenite dehydrate is performed by adding selenius acid (H2SeO3) with basic cobalt (II) carbonate (Co (OH2)2 CO3) or platinum carbonate (Pt (OH2) 2 CO3). Basic cobalt (II) carbonate (Co (OH2)2 CO3) or platinum carbonate (Pt (OH2) 2 CO3) solutions were prepared by mixing equimolar amounts of CoCl2 or PtCl2 (cobalt or platinum chloride) and Na2CO3 (sodium carbonate). The solid precipitate of Cobalt carbonate (precipitate 3) was washed till the absence of foreign ions.

$$2H_2O+CoCl_2+Na_2CO_3 \rightarrow CoCO_3.2H_2O+2NaCl \quad \text{(Eq 2)}$$

An aqueous solution of $H_2SeO_3$, 2 g in 10 ml water (0.016 mol) was added to a warm solution of the freshly prepared Cobalt (Co) carbonate, 1.22 g in 10 ml water (0.008 mol). The Co carbonate and $H_2SeO_3$ mixed solution is then filtered and kept at room temperature for crystallization. It was observed that after 2 days crystalline prisms of red color crystals were formed. The crystals were first filtered, washed with water and dried in air.[18] For obtaining platinum (II) hydrogen selenite dihydrate an aqueous solution of 2 g $H_2SeO_3$ in 10 ml water was added to a warm solution of the freshly prepared Pt carbonate (precipitate 4) 1.28 g in 10 ml water. The obtained solution is filtered and kept at room temperature for crystallization after 24 hour; crystalline prisms of blue color are formed. The temperature of removal of 2 molecules of water is 100-110° C.

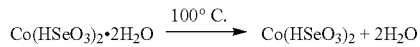
$$Co(HSeO_3)_2 \cdot 2H_2O \xrightarrow{100°\ C.} Co(HSeO_3)_2 + 2H_2O$$

Synthesis of Cobalt or Platinum Fatty Olylammonium Hydrogen Selenite Complexes:

Cobalt or platinum fatty olylammonium hydrogen selenite complexes were prepared by refluxing two moles of olylammonium hydrogen selenites ($II_a$) with one mole of cobalt or platinum hydrogen selenite in ethyl alcohol for two hours. The product 1 or 2 is designated as ($IIb$ and $IIc$).

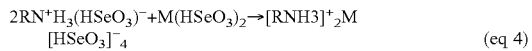
$$2RN^+H_3(HSeO_3)^- + M(HSeO_3)_2 \rightarrow [RNH3]^+_2 M[HSeO_3]^-_4 \quad (eq\ 4)$$

The product 1 or 2 is purified and recrystallized three times in petroleum ether and then washed with diethyl ether. The products kept in desiccators till used. General formula for the metal complexes may be shown as below:

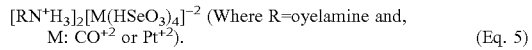
$$[RN^+H_3]_2[M(HSeO_3)_4]^{-2}\ (\text{Where R=oyelamine and, M: } Co^{+2}\ or\ Pt^{+2}). \quad (Eq.\ 5)$$

Method of Making the Nanoparticle Comprising of Cyclodextrin and Olylammonium Hydrogen Selenite Co/Pt Complex:

The Co or Pt complex was mixed mechanically very well with the cyclodextrin oligosaccharide using vortex then both are ground to the nano sized particles using ball mill model PM 400 at 200 rpm for 10 hours. Planetary Ball Mills are used wherever the highest degree of finesse is required. Apart from the classical mixing and size reduction processes, the mills also meet all the technical requirements for colloidal grinding and have the energy input necessary for mechanical alloying processes. The extremely high centrifugal forces of the Planetary Ball Mills result in very high pulverization energy and therefore short grinding times. The product loaded cyclodextrin complex nanoparticles was obtained and their particle size was determined using transmission electron microscope.

FIG. 1 shows the nanoparticle comprising of cyclodextrin and Co complex. The compound is oyelamine hydrogen selenite cobalt complex but for simple form we can say Co complex, then we comprising it with cyclodextrin (In the pharmaceutical industry, cyclodextrins have mainly been used as compressing agents to increase the grinding ability and the aqueous solubility of poorly water-soluble drugs, and to increase their bioavailability and stability. In addition, cyclodextrins can be used to reduce gastrointestinal and ocular irritation, reduce or eliminate unpleasant smells or tastes, prevent drug-drug or drug-additive interactions, or to convert oils and liquid drugs into microcrystalline or amorphous powders.

TABLE 1

The critical micelle concentration (CMC) and surface parameter ammonium hydrogen selenite surfactants

| Comp. | CMC × $10^{-3}$ | $\gamma$CMC (mN/m) | $\Pi$CMC (mN/m) | PC20 (Mole/L) | $\Gamma$max × $10^{-11}$ (Mole/cm$^2$) | A min (nm2) | $\Delta$ Gads | $\Delta$ Gmic | $\Delta$ Gads/ Amin |
|---|---|---|---|---|---|---|---|---|---|
| IIa | 1.3 | 33 | 39 | 3.8 | 10.6 | 1.6 | −67.7 | −34.1 | −46.8 |
| IIb | 1.1 | 32 | 40 | 4.0 | 10.8 | 1.5 | −69.9 | −34.8 | −49.1 |
| IIc | 0.70 | 30 | 42 | 4.1 | 11.3 | 1.45 | −71.1 | −35.3 | −50.2 |

As shown from previous table by complexing parent surfactants with cobalt or platinum ions, high depression was observed in CMC values. That fact could be explained from the unique property of the metal complexes in water. That is the complexes retain its unity in their solutions, which increased their volume in the aqueous media and then repulsion is occurred between the hydrophobic chain and water molecules. (IIc) was found to be the most efficient one in because it achieved the maximum reduction of the surface tension at CMC. The efficiency "PC20" increase with increasing molar ratio of methylene units. These due to the fact that the efficiency of adsorption at interfaces increase linearly with increase in the carbon atoms in hydrophobic group. In case of the prepared parent cationic surfactants by increasing the number methylene units Maximum surface excess $\Gamma$max increases, this due to migration of molecules to the water-air interface. The consequence increase of $\Gamma$max leads to crowdiness occurred at the interface which causing decrease in Minimum area per molecule Amin values. That is due to the minimum surface area decrease with increasing the hydrophobic chain length of the synthesized surfactant molecules. The standard free energies of micellization $\Delta G°$ mic and adsorption $\Delta G°$ ads values are always negative indicating the spontaneously of these two processes but there is more increase in negativity of $\Delta G°$ ads rather than those of micellization indicating the tendency of the molecules to be adsorbed at the interface.

Antitumor Action of the Prepared Compounds:

Olylammonium hydrogen selenites hydrogen selenite with its cobalt and platinum complexes were investigated as potential selective, anticancer prodrugs. They were tested by using Ehrlich Acites Carcinoma (EAC) as a model system of mice cell tumor. These compounds were also Tested in vitro on human five monolayer tumor cell lines: MCF7 (Breast carcinoma), HEPG2 (liver carcenoma), U 251 (Hela tumor) and HCT116 (colon carcinoma).

Evaluation of Antitumor Activity of the (EAC):

Ehrlich ascites carcinoma cells as a model system was based on the finding that it is excellent tool for studying the biological behavior of malignant tumors and drug action with cells. A line of Ehrlich ascites carcinoma (EAC) which used in the present study had been kindly supplied from National Cancer Institute, Cairo, Egypt, and maintained in female Swiss albino mice through weekly IMP transplantation of 2.5×106 tumor cells/mouse. EAC cells were obtained by needle aspiration with aseptic condition. The ascetic fluid was diluted with sterile saline so that 0.1 ml contains 2.5×106 cells counted microscopically using a haemocytometer. In vitro studying of these compounds antitumor activity was determined according to the percentage of nonviable cells (NVC %) which was calculated by the following equation NVC %=[number of NVC/total number of cells]/100.

TABLE 2

Antitumor activity of the prepared compounds using (EAC):

| Sample | | % Inhibition of cell viability µg/ml | |
|---|---|---|---|
| Conc. µg/ml | 100 | 50 | 25 |
| IIa | 40% | 20% | 10% |
| IIb | 100% | 80% | 40% |
| IIc | 90% | 70% | 30% |

As shown from Table 2 increasing the concentration of olylammonium hydrogen selenite (IIa) and its cobalt (IIb) or platinum (IIc) complexes in the EAC media was accompanied by progressive increase in the percent of non-viable cells. This comes from the fact that by increasing the concentration of cationic surfactant the adsorption of ions on cell membrane increases, leading to increase in penetration and antitumor activity. The inhibition of cell viability percent showed that the IIb (cobalt complex) is the most active one at concentration 100 µg/ml, the percentage of non-viable cell reach to 100%. This mean that the drug at this concentration cause death all the tumor cell while, at concentration 50 µg/ml the percentage of reach to 80%. But, at concentration 25 µg/ml the (NVC %) reach to 40%. While IIc (platinum complex) at concentration 100-µg/ml (NVC %) reach to 90% and at concentration 50 µg/ml reach 70%. From these results IIa,c are the most active of all derivatives, since cobalt complexes seem to offer promise due to high electron affinity of the metal which increasing the ability to bind DNA and the ready reducibility of the compounds. While, it can be seen that IIa has the least toxic effect of all derivatives on EAC cells.

Evaluation of Cytotoxic Activity on Human Tumor Cell Lines:

The results of the cytotoxic activity on human tumor cell lines were determined according to the dose values of drug exposure for cell lines to reduce survival to 50% (Ic50). The experimental results recorded in Table (3).

TABLE (3)

Cytotoxic activity of the IIb,c compounds on human cell line

| | Cell lines | | | |
|---|---|---|---|---|
| Sample | HELA (IC50) | MCF7 (IC50) | HEPG2 (IC50) | HCT116 (IC50) |
| IIb | 2.08 | o.6 | 0.94 | −Ve |
| IIc | −Ve | 0.47 | 1.41 | −Ve |

The compounds tested exhibited high activity in vitro system on the tumor cell line investigated, IIb have the highest cytotoxic effect on MCF7, HEPG2 and HELA. The dose of it at which the survival reduction to 50% is (Ic50=0.6, 0.94 and 2.8 µg/ml), respectively. Also IIc show good cytotoxic activity on HEPG2 and MCF7 (Ic50=1.41 and 0.47 µg/ml), respectively. It should be noted that the action of these compounds as antitumor agents found to be dependent on the type of tumor cell line tested, but as shown from the results IIb (cobalt complexes) show excellent cytotoxic activity against several tumor cell line and under very low concentration reduces the survival to 50%. This comes from the fact that cobalt complexes have a capacity to reduce the energy status in tumors as well as enhance the tumor hypoxia which also influences their antitumor activities. It may be also concluded that the level of cellular damage inflicted by these complexes depends on the nature of their axial ligands. There is evidence that cobalt complexes cause significant changes in metabolism namely activation of lipid peroxidation, DNA damage and reduction of the bioenergetic status of tumor tissues. In general high selectivity of action by redox—active cobalt complexes upon tumors is due to their specific reactivity. Platinum complexes exhibit superoxide dismutase like activity which used as anti-inflammatory agent and lipid soluble. This property enables the compound to penetrate membranes and become inter-cellular. Finally platinum and cobalt complex surfactant nanoparticles in our research affect tumor tissue at very low concentration at values lower than their CMC values, which mean that there is a strong relation between very small values of CMC of these compounds and the reaching to Ic50 values under very low concentration, this due to the fact that increasing concentration of cationic surfactant causes increase the adsorption process on cell membrane till reaching the CMC, after this concentration the adsorption retarded slowly then stopped due to form micelles which prevent the mobility and suppress antitumor activity. Oyelammonium hydrogen selenite does not reach to Ic50 for all tested human monolayer tumor cell lines. Many targets may be explored to counteract cancer and indication the role of studied metals should be useful for a better use of metal-based anticancer drugs.

Antibacterial Activity of the Prepared Surfactants Against Sulphur Reducing Bacteria:

Sulphur reducing bacteria are mainly sulfate reducers, and their growth frequently causes severe corrosion problems in oil well pipes. Due to the economic losses as well as environmental health and safety hazards caused by the activity of stabilized mixed culture containing sulphate reducing bacteria, (SMC-SRB) in many industrial sectors such as the oil and gas industry, it was important to minimize the risks resulting from SRB activity.

Sulfur reducing bacteria are strict anaerobes that are often found in biotopes where toxic conditions can temporarily existing. The bacteria have developed several defense strategies in order to survive exposure to oxygen. These strategies include peculiar behaviors in the presence of oxygen, like aggregation or aerotaxis, and enzymatic systems dedicated to the reduction and the elimination of oxygen and its reactive species.

Quaternary ammonium compounds are most effective against anaerobic bacteria (e.g. those that occur in oil wells). Several studies indicated that some quaternary ammonium compounds act as corrosion inhibitors and decrease sulfide production by (SRB) at low concentration than some biocides of commercial source. The results of the synthesized cationic surfactants against sulphur reducing bacteria recorded in Table 4.

TABLE 4

Inhibition zone diameter (mm/mg sample) for the synthesized cationic surfactants against sulphur reducing bacteria.

| Sample | Inhibition zone diameter (mm/mg sample) Sulphur reducing bacteria |
|---|---|
| IIa | 25 |
| IIb | 24 |
| IIc | 23 |

The results in Table 4 indicates that the new synthesized cationic surfactants have high antimicrobial activity against sulphur reducing bacteria, and the difference in activity depends on the length of hydrophobic chain. The optimal length of the alkyl chain has been noted to be ten carbon atoms. The highest results were achieved by platinum complexes, this may be due to platinum is oxidizing agent act as reduction inhibitors leading to decrease in sulfide production and decreasing the growth rate of anaerobic (SRB). In more general bacterial growth Inhibition by metal ions was investigated in the sulphate-free medium. The rate of $H_2S$ production was approximately directly proportional to the specific activities of the invested enzymes. These activities were inversely proportional to the generation time. The rate of microbiologically induced corrosion (MIC) of carbon steel was directly proportional to bacterial resistance to metal ions.

The technological advancement of this invention is novel for the complex to be used as antitumor agent. In addition, it will be appreciated that the various compounds for making the complex nano particle and method of using the complex nano particle such as antibacterial activity or antitumor activity can be made. Accordingly, the specification and drawings are to be regarded in an illustrative rather than a restrictive sense.

What is claimed is:

1. A process to make a nanoparticle complex to reduce a cell viability, comprising:
   mixing stoichiometric amounts of a selenius acid and olylamine in an ethyl alcohol, stirring the solution till a precipitate is formed;
   filtering and washing the precipitate by ethyl alcohol;
   crystallizing the precipitate by diethyl ether to form a olylammonium hydrogen selenite reacting a sodium carbonate with a metal carbonate forming a metal carbonate precipitate;
   refluxing two moles of the olylammonium hydrogen selenite to one mole of the metal carbonate to form a metal olylammonium hydrogen selenite complex; and
   mixing and grounding a cyclodextrin and the metal olylammonium hydrogen selenite complex to form the nanoparticle complex of cyclodextrin-metal olylammonium hydrogen selenite complex of a specific size to be used as an anti-tumor agent.

2. The process of claim 1, wherein the precipitate is recrystallized by diethyl ether.

3. The process of claim 1, wherein olylammonium hydrogen selenites formed has a general formula $RN^+H_3HSeO_3$.

4. A process, comprising:
   reacting a selenius acid with a metal carbonate forming a precipitate;
   washing the precipitate followed by a filtration;
   leaving a filtrate at room temperature for crystallization;
   washing a crystal formed with water;
   drying the crystals in air and forming metal complex as a metal hydrogen selenite dehydrate complex
   and mixing the metal olylammonium hydrogen selenite dehydrate complex with a cyclodextrin oligosaccharide to form a nanoparticle as a metal based cationic surfactant to be used as an anti-cancer drug.

5. The process of claim 4, wherein metal hydrogen selenite dehydrate complex is a Cobalt hydrogen selenite dehydrate complex.

6. The process of claim 4, wherein metal hydrogen selenite dehydrate complex is a Platinum hydrogen selenite dehydrate complex.

7. The process of claim 4, wherein selenius acid and Platinum carbonate is mixed in equimolar amounts to form Platinum hydrogen selenite dehydrate complex.

8. The process of claim 4, wherein selenius acid and Cobalt carbonate is mixed in 1:2 ratio to forma Cobalt hydrogen selenite dehydrate complex.

9. The process of claim 4, wherein the filtrate is left for 2 days for crystallization for the formation of a Cobalt hydrogen selenite dehydrate complex.

10. The process of claim 4, wherein the filtrate is left for 24 hours for crystallization for the formation of a Platinum hydrogen selenite dehydrate complex.

* * * * *